United States Patent [19]

Imokawa et al.

[11] 4,139,485

[45] Feb. 13, 1979

[54] DETERGENT COMPOSITION

[75] Inventors: Genji Imokawa, Wakayama; Hisao Tsutsumi, Sakura; Tomihiro Kurosaki, Osaka; Makoto Hayashi; Junko Kakuse, both of Wakayama, all of Japan

[73] Assignee: Kao Soap Co., Ltd., Tokyo, Japan

[21] Appl. No.: 770,455

[22] Filed: Feb. 22, 1977

[30] Foreign Application Priority Data

Aug. 24, 1976 [JP] Japan .................................. 51-101004

[51] Int. Cl.² .......................... C11D 3/36; C11D 7/36
[52] U.S. Cl. ................................ 252/135; 252/89 R; 252/135; 252/DIG. 13; 252/DIG. 16
[58] Field of Search ......... 252/89, 135, 136, DIG. 13, 252/DIG. 16; 260/924

[56] References Cited

U.S. PATENT DOCUMENTS

| 3,538,197 | 11/1970 | Vilsmeier | 252/89 X |
|---|---|---|---|
| 3,584,087 | 6/1971 | Mausner et al. | 252/89 XL |
| 4,018,696 | 4/1977 | Hellsten et al. | 252/89 R |

*Primary Examiner*—Mayer Weinblatt

*Attorney, Agent, or Firm*—Blanchard, Flynn, Thiel, Boutell & Tanis

[57] ABSTRACT

A detergent composition which has a low irritation effect to human skin containing as an active surfactant component one or a mixture of compounds having the formulas

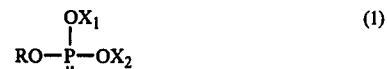

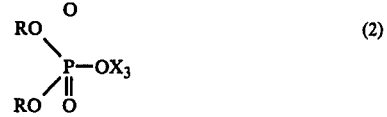

wherein R is saturated or unsaturated hydrocarbon having 10 to 16 carbon atoms, $X_1$ and $X_3$ are hydrogen, alkali metal, ammonium, alkylammonium or substituted alkylammonium, and $X_2$ is alkali metal, ammonium, alkylammonium or substituted alkylammonium, with the provisos that both $X_1$ and $X_2$ are not alkali metal and that when R has an average carbon atom number of 10, $X_1$ is hydrogen, and wherein the weight ratio of the formula (1) compound(s) : formula (2) compound(s) is from 100:0 to 80:20.

13 Claims, No Drawings

DETERGENT COMPOSITION

BACKGROUND OF THE INVENTION

1. FIELD OF THE INVENTION

The present invention relates to a low skin irritation detergent composition containing, as an active surfactant ingredient, a monoalkyl phosphate salt.

2. DESCRIPTION OF THE PRIOR ART

As surfactant components of detergent compositions, there have been widely used anionic surfactants such as alkyl sulfates, polyoxyethylene alkyl sulfates, alkylbenzene sulfonates and α-olefin sulfonates.

It is known that such anionic surfactants are adsorbed and thereby remain on the skin surface to cause dryness and scaling of the epidermis, or skin chapping and roughness, if they are used continually. Thus, skin troubles such as roughness of hands are apt to be caused by the use of detergents. Skin roughness can be a precursor of more severe skin troubles such as housewife's eczema. Thus, there is an urgent need to eliminate this disadvantage.

On the other hand, non-ionic surfactants, unlike anionic surfactants, cause little or no skin roughness. However, their properties as surfactants, such as foaming power and detergency, are far inferior to the corresponding properties of anionic surfactants and it has been unsuitable, for many purposes, to incorporate them as detergent active ingredients into detergent compositions.

Further, although phosphoric ester surfactants have been known as anionic surfactants, the phosphoric ester surfactants heretofore used are merely mixtures of mono- and diesters or mixtures of mono-, di- and triesters and, therefore, their water-solubilities are very low and they do not possess adequate deterging and foaming powers. In addition, incorporation of them in detergent compositions is difficult.

Although surfactant compounds to which ethylene oxide has been adducted for improving water solubility have also been known, their foaming and deterging powers are also poor and incorporation thereof in detergent compositions has been difficult.

It has been considered that skin roughness is caused mainly by a skin film removing action due to a defatting action and, therefore, the higher the deterging power of the detergent composition, the stronger is the skin roughening action. Thus, it has been considered that it is impossible to obtain detergent compositions that possess a comparatively excellent deterging power and exhibit a low skin roughening effect. The skin roughness referred to herein signifies dryness and scaling of the epidermal layer and is distinguished from skin irritation indicating inflammatory changes such as redness, papula and edema.

However, after intensive investigations, we have discovered that factors which have an influence on the skin roughness include not only the power of the detergent composition for defatting the epidermis, but also many other factors such as its keratin protein denaturating power, skin lysosome and membrane-weakening power. It is more important that the power of the detergent active ingredient to absorb and remain on the skin epidermal layer has a close relationship to the above factors, because the step of washing the detergent off the skin, in running water, is normally practiced after use of the detergent for cleaning has been completed.

It has been considered, therefore, that the degree of skin roughness can be reduced, while maintaining the deterging properties, provided that the keratin protein denaturation and adsorbing/remaining power of the detergent are reduced while the deterging power is kept strong.

For attaining this object, we have investigated structures of surfactants which can reduce the adsorbing/remaining power on the epidermal layer and the power of denaturating keratin proteins and discovered that it is possible to prepare surfactants having excellent surface active properties and reduced adsorbing/remaining power and keratin protein-denaturating power by introducing therein a phosphate group, in place of the terminal sulfate or sulfonate group of the conventional anionic surfactants.

SUMMARY OF THE INVENTION

We have discovered that a detergent composition possessing excellent deterging and foaming powers, but which is free from serious skin roughening effects, can be obtained by incorporating a monoalkyl phosphate salt in the detergent composition.

The detergent composition of the present invention contains as a principal detergent active ingredient one or a mixture of two or more monoalkyl phosphate salt(s) of formula (1) and dialkyl phosphate ester salt(s) of formula (2) in a weight ratio of 100:0 to 80:20:

wherein R is a saturated or unsaturated hydrocarbon radical having an average carbon number of 10 to 16, $X_1$ and $X_3$, which can be the same or different, each is a member selected from the group consisting of hydrogen, alkali metal, ammonium, alkylammonium and substituted alkylammonium, $X_2$ is a member selected from the group consisting of alkali metal, ammonium, alkylammonium and substituted alkylammonium ion, with the provisos that $X_1$ and $X_2$ cannot both be an alkali metal simultaneously, that when R is a hydrocarbon having an average carbon number of 10, $X_1$ is H, and that the compounds have a Krafft point of less than 55° C. and aqueous solutions thereof have a pH of 5 to 9.

Monoalkyl phosphate salts of formula (1) can be prepared, for example, by a known process wherein a long chain aliphatic alcohol is reacted with a phosphatizing agent such as phosphoric anhydride or phosphorus oxychloride. The dialkyl phosphate of formula (2) which may be by-produced by this process possesses poor water-solubility or foaming property. Accordingly, the weight ratio of the monoalkyl phosphate salt of formula (1) to the dialkyl phosphate salt of formula (2) is from 100:0 to 80:20, preferably from 100:0 to 90:10, particularly preferably substantially 100:0.

Compositions which are not within the proportion of monoalkyl phosphate salt to dialkyl phosphate salt of from 100:0 to 80:20, such as sesquialkyl phosphate salts, are not within the scope of the present invention.

The surfactants of the present invention are particularly useful in detergent products which are directly contacted with the skin for a long time such as shampoos and solid synthetic detergent toilet bars, because they have a characteristic, excellent foaming power and skin roughness is not caused. The surfactants may also be used as ingredients of dish-washing liquid detergents, powder detergents and dentifrices.

The saturated and unsaturated hydrocarbon groups having an average carbon number of 10-16 (R in formulas (1) and (2) are straight chain, branched or alicyclic hydrocarbons such as decyl, undecyl, dodecyl, tridecyl, tetradecyl, pentadecyl and hexadecyl groups and corresponding olefinically unsaturated groups. Those hydrocarbon groups are contained in the compositions singly or in the form of a combination of several groups. Saturated hydrocarbon groups of an average carbon number of 10 to 14 and unsaturated hydrocarbon groups of an average carbon number of 16 are particularly preferred.

The preferred alkali metals for $X_1$, $X_2$ and $X_3$, according to the invention, are, for example, lithium, sodium and potassium.

The alkylammonium or substituted alkylammonium for $X_1$, $X_2$ and $X_3$, according to the invention, are cations produced from amines used for neutralization of the corresponding phosphoric acids by quaternization after the neutralization step in the process for preparing monoalkyl phosphate salts of formula (1). The corresponding amines are primary, secondary and tertiary amines having alkyl groups of 1 to 3 carbon atoms which may be further substituted, particularly by hydroxyl groups. As the amines, there may be mentioned, for example, dimethylmonoethanolamine, methyldiethanolamine, trimethylamine, triethylamine, dibutylamine, butyldimethylamine, monoethanolamine, diethanolamine, triethanolamine, isopropyldimethylamine and isopropylethanolamine. Preferred amines are monoethanolamine, diethanolamine and triethanolamine. A particularly preferred amine is triethanolamine.

The aqueous solutions having a pH in the range of 5 to 9 herein mean that 3 wt.% aqueous solutions of the alkyl phosphate salts according to the invention have a pH in the range of 5 to 9 at room temperature. If both $X_1$ and $X_2$ in the compound of formula (1) are alkali metal, the pH thereof is above 9.5, and such cause strong irritation of skin. Such compounds are not included in the invention. Further, a compound having a pH below 5 is unsuitable for detergents due to the too strong acidity thereof.

Some properties of following typical compounds a) f), according to the present invention, are shown in Table 1.

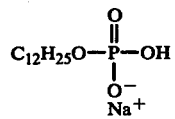

a)

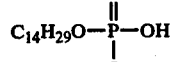

b)

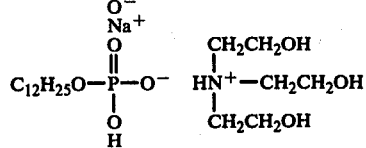

c)

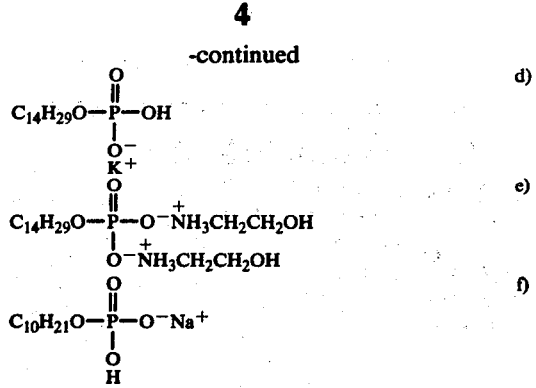

d)

e)

f)

Table 1

| Sample | a | b | c | d | e | f |
|---|---|---|---|---|---|---|
| Properties of Compounds | | | | | | |
| Appearance | White powder | White powder | White powder | White powder | White powder | White powder |
| Water-solubility | Good | Good (but less than sample a) | Good | Good (but less than sample a) | Good | Good |
| Odor | Substantially none | Substantially none | Substantially none | Substantially none | Substantially none | Substantially none |
| pH | 6.5 | 6.6 | 6.4 | 6.0 | 7.5 | 5.8 |

The relationship between (1) the carbon number of the alkyl group and the cation and (2) Krafft point, foaming property and solubility of monoalkyl phosphate salts of formula (1) are shown in Tables 2 to 5.

Table 2

Krafft Point and Foaming Power of $RO-\underset{\underset{O}{\|}}{\overset{OH}{\underset{|}{P}}}-ONa$ ($X_1$ = H, $X_2$ = Na)

| Alkyl Group (R) | Krafft Point (° C)[1] | Foaming Power (mm) 40° C[2] | Solubility |
|---|---|---|---|
| n-Decyl | Less than 10 | 220 | 1 |
| Lauryl | 30 | 240 | 1 |
| Myristyl | 55 | 200 | 2 |
| Palmityl | 66 | 50 | 3 |
| Stearly | Above 90 | Less than 50 | 3 |
| n-Eicosyl | Above 90 | Less than 50 | 3 |

Table 3

Krafft Point and Foaming Power of $RO-\underset{\underset{O}{\|}}{\overset{ONa}{\underset{|}{P}}}-ONa$ ($X_1$ = Na, $X_2$ = Na)

| Alkyl Group (R) | Krafft Point (° C) | Foaming Power (mm) | Solubility |
|---|---|---|---|
| n-Decyl | Less than 10 | 60 | 1 |
| Lauryl | " | 120 | 1 |
| Myristyl | 28 | 230 | 1 |
| Palmityl | 45 | — | 2 |
| Stearyl | 57 | — | 3 |
| n-Eicosyl | 65 | — | 3 |

Table 4

Krafft Point and Foaming Power of $RO-\underset{\underset{O}{\|}}{\overset{OH}{\underset{|}{P}}}-OK$ ($X_1$ = H, $X_2$ = K)

| Alkyl Group (R) | Krafft Point (° C) | Foaming Power (mm) | Solubility |
|---|---|---|---|
| n-Decyl | Less than 10 | 190 | 1 |

Table 4-continued

Krafft Point and Foaming Power of 
$$RO-\underset{\underset{O}{\|}}{\overset{\overset{OH}{|}}{P}}-OK$$

($X_1$ = H, $X_2$ = K)

| Alkyl Group (R) | Krafft Point (° C) | Foaming Power (mm) | Solubility |
|---|---|---|---|
| Lauryl | " | 230 | 1 |
| Myristyl | 35 | 210 | 1 |
| Palmityl | 47 | 160 | 2 |
| Stearyl | Above 60 | — | 3 |
| n-Eicosyl | Above 60 | — | 3 |

Table 5

$$RO-\underset{\underset{O}{\|}}{\overset{\overset{OH}{|}}{P}}-\overset{\overset{H}{|}}{O}N-(C_2H_4OH)_3 \quad (X_1 = H, X_2 = \overset{(+)}{H}N(C_2H_4OH)_3)$$

| Alkyl Group (R) | Krafft Point (° C) | Amount of Foams (ml)[4] | Solubility |
|---|---|---|---|
| n-Decyl | Less than 10 | — | 1 |
| Lauryl | " | 240 | 1 |
| Myristyl | " | 220 | 1 |
| Palmityl | 30 – 50 | — | 2 |
| Stearyl | Above 60 | — | 3 |
| n-Eicosyl | Above 60 | — | 3 |

Note:
(1) Krafft point is a point of bending of a curve obtained by determination of the relationship between equivalent conductivity and temperature by using an electric conductivity meter.

(2) Foaming power was determined at a dilution of 1/40 at 40° C. by the Ross-Miles method.

(3) Solubility is shown by the following three ranks:
1 ... Completely soluble in water and effective as foaming agent
2 ... Dispersible in water to form a stable dispersion and effective as foaming agent
3 ... Insoluble in water and ineffective as a foaming agent (4) Amount of foams was determined as follows: 0.1% of lanolin as artificial soil was added to 0.5% aqueous solution of the detergent composition and the mixture was stirred in a cylinder with a flat propeller at a speed of 1,000 rpm. at 25° C. for 5 minutes and reversing the direction of rotation of the propeller at intervals of 10 seconds. 30 seconds after completion of the stirring, the amount of foam was determined.

Although alkyl phosphate salt mixtures wherein the alkyl groups have large average carbon numbers, i.e. those having high Krafft points, can be used according to the present invention, those having Krafft points of less than 55° C. are preferred, because at a Krafft point of higher than 55° C., the foaming power is poor. Alkyl phosphate salts wherein the alkyl groups have an average carbon number of 9 or less or monoalkyl phosphate salts of formula (1) wherein $X_1$ is a group other than H when the alkyl groups have an average carbon number of 10, have a very poor foaming property and are not included within the scope of the invention.

Monoalkyl phosphate salts of formula (1) wherein the alkyl groups are saturated straight chain alkyl groups are shown in Table 6 wherein (C) indicates acceptable salts. (B) indicates more preferred salts, (A) indicates the most preferred salts and (D) indicates those not covered by the present invention.

Table 6

Example of Preferred Range of Monoalkyl Phosphate Salts

| | $X_1$ | $X_2$ | Average Carbon Number of R | | | | | |
|---|---|---|---|---|---|---|---|---|
| | | | 10 | 12 | 14 | 16 | 18 | 20 |
| Cation | TEA* | TEA* | D | B | B | C | D | D |
| | K | K | D | D | D | D | D | D |
| | Na | Na | D | D | D | D | D | D |
| | H | TEA | B | A | B | C | D | D |
| | H | K | B | A | B | C | D | D |
| | H | Na | B | A | B | C | D | D |

*TEA = Triethanolamine

The following examples further illustrate the present invention. In these examples the term "%" means weight percent.

EXAMPLE 1

For examining the effect of the pH of aqueous solutions of compounds (1) of the invention on human skin irritation, a closed patch test was effected for 24 hours by using 3% aqueous solutions of the compounds shown in Table 7, the pH of which was varied by adding NaOH.

The degree of skin irritation was evaluated by dividing the results into seven total ranks, i.e. redness (± to ++), edema (± to ++) and "negative", two hours after removal of the patch. Scores of ±(0.5), +(1.0) and ++(2.0) were given and the total scores of redness and edema were employed as a standard of skin irritation (skin irritation index). The results are shown in Table 7.

Table 7

| Sample | pH (3%) | Skin Irritation (Score) |
|---|---|---|
| $C_{12}H_{25}O-\underset{\underset{ONa}{\|}}{\overset{\overset{O}{\|}}{P}}-OH$ | 6.4 | 0.0 |
| " | 7.0 | 0.5 |
| | 9.8 | 12.0 |
| $C_{12}H_{25}O-\underset{\underset{ONa}{\|}}{\overset{\overset{O}{\|}}{P}}-ONa$ | | |
| $C_{14}H_{29}O-\underset{\underset{ONa}{\|}}{\overset{\overset{O}{\|}}{P}}-OH$ | 7.0 | 1.0 |
| " | 8.0 | 1.5 |
| | 10.9 | 14.5 |
| $C_{14}H_{29}O-\underset{\underset{ONa}{\|}}{\overset{\overset{O}{\|}}{P}}-ONa$ | | |

It is apparent from Table 7 that those having a pH above 9 (3%) exhibit a strong undesirable skin irritation and, therefore, they are not within the scope of the invention.

EXAMPLE 2

Foaming test and water-solubility test were carried out by using the following detergent compositions:

| | Weight Ratio of Compound of formula (1) below, to Compound of formula (2) below | |
|---|---|---|
| a | 100 : | 0 |
| b | 90 : | 10 |
| c | 80 : | 20 |
| d | 70 : | 30 |
| e | 60 : | 40 |
| f | 50 : | 50 |
| g | 40 : | 60 |
| h | 30 : | 70 |

-continued

| | Weight Ratio of Compound of formula (1) below, to Compound of formula (2) below | |
|---|---|---|
| i | 20 : | 80 |
| j | 10 : | 90 |
| k | 0 : | 100 |

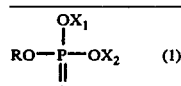 (1)

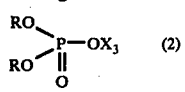 (2)

In the foaming test, 0.1% of lanolin as an artifical soil was added to 0.5% aqueous solution of the composition and the mixture was stirred in a cylinder with a flat propeller at a speed of 1,000 rpm at 25° C. for 5 minutes and the direction of rotation of the propeller was reversed at intervals of 10 seconds. 30 seconds after completion of the stirring, the amount of foam was determined to determine the foaming power. Water-solubility was evaluated from the appearance of 1% aqueous solution of the composition at 25° C. The results are shown in Table 8.

Table 8

| | | Foaming Property and Solubility in Water | | | | | | | | |
|---|---|---|---|---|---|---|---|---|---|---|
| R in formula (1) $X_1, X_2$ in formula (1) R in formula (2) $X_3$ in formula (2) | | n-$C_{10}H_{21}$ H,Na n-$C_{10}H_{21}$ Na | | n-$C_{12}H_{25}$ H,Na n-$C_{12}H_{25}$ Na | | n-$C_{14}H_{29}$ H,TEA n-$C_{14}H_{29}$ TEA | | iso-$C_{12}H_{25}$ H,Na iso-$C_{12}H_{25}$ Na | | *iso-$C_{18}H_{37}$ K,K iso-$C_{18}H_{37}$ K |
| | Weight ratio of (1) to (2) | Amount of foams (ml) | Water-solubility | Amount of foams (ml) | Water-solubility | Amount of foams (ml) | Water-solubility | Amount of foams (ml) | Water-solubility | Amount of foams (ml) | Water-solubility |
| Composition of the invention | a | 185 | Transparent | 204 | Transparent | 242 | Transparent | 185 | Transparent | 105 | Transparent |
| | b | 164 | " | 202 | " | 240 | " | 178 | " | 103 | " |
| | c | 146 | " | 202 | " | 237 | " | 169 | " | 101 | " |
| | d | 125 | " | 197 | Slightly turbid | 125 | Turbid | 142 | Slightly turbid | 95 | " |
| | e | 48 | Slightly turbid | 32 | Turbid | 57 | " | 37 | Turbid | 33 | " |
| Comparative Composition | f | 25 | Turbid | 5 | " | 24 | " | 0 | " | 12 | Turbid |
| | g | 3 | " | 0 | " | 7 | " | 0 | " | 0 | " |
| | h | 0 | " | 0 | " | 0 | " | 0 | " | 0 | " |
| | i | 0 | " | 0 | " | 0 | " | 0 | " | 0 | " |
| | j | 0 | " | 0 | " | 0 | " | 0 | " | 0 | " |
| | k | 0 | " | 0 | " | 0 | " | 0 | " | 0 | " |

*Comparative example

It is apparent from the results shown in Table 8 that compositions comprising compounds of formulas (1) and (2) in a weight ratio in the range of from 100:0 to 80:20 exhibit an excellent foaming power and a high water water solubility, whereas the compositions containing less than 80% of (1) have far inferior foaming properties and water solubility and they are unsuitable for use in the detergent compositions of the invention. Thus, the latter are not within the scope of the invention.

EXAMPLE 3

Skin roughness (dryness and scaling on skin surface) was examined by a circulation method with 1 wt.% aqueous solutions (adjusted to pH 7.0) of compounds (a)—(f) according to the invention and nine other comparative compounds. The results are shown in Table 9.

Circulation method is effected as follows:

150 ml of each of three different 1% aqueous solutions (pH 7.0) of surfactants are put in three glass containers and kept at 37° C. Then, three glass caps are placed close to each other adjacent the elbow of the forearms of test subjects. A rubber cap is fitted to the bottom of each of the three caps for increasing adhesion to the skin. The caps are then connected with the glass vessels containing the aqueous solutions of the surfactants, together with a circulator and a silicon tube. The circulator is operated to circulate 150 ml of the aqueous solutions of the three surfactants simultaneously through the silicon tube at a rate of 200 ml/min. The skin surface attached with the caps is thus washed for 10 minutes. After washing, the forearms are immersed four times in a sufficient quantity of city water in a tank in order to wash the treated region. The above procedure is repeated once a day for four days and the change of the skin in the capped regions is observed every morning with the naked eye until the fifth morning.

The skin change caused by the circulation method is called "roughness". The roughness is evaluated on the basis of the following four ranks:

± ... Slight scaling change and gloss are observed.
+ ... Moderate scaling change and gloss are observed.
++ ... Strong scaling and gloss are observed.
− ... No change.

Scores are assigned based on number of times (1–4 times) of circulations required until roughness appears as follows:

| Number of times | Score |
|---|---|
| 1 | 4 |
| 2 | 3 |
| 3 | 2 |
| 4 | 1 |

The scores are combined with other scores of degree of roughness observed at that time ("negative" = 0, "±" = 0.5, "+" = 1.0, "++" = 2.0). The sum of the scores divided by number of subjects (average of the subjects) is employed as an index of the skin roughness (average skin roughness index). For example, if three subjects comprise one subject of "roughness +" after circulation once and two subjects of "roughness ++" after circulation twice, the scoe will be as follows:

(4 × 1.0 + 3.0 × 2.0 × 2) ÷ 3 = 5.33

Inflammatory change is determined as follows: If roughness is advanced in the determination of skin chapping by the circulation method, the skin surface becomes red and then inflamed. The number of subjects with the inflammation is divided by number of subjects subjected to the circulation method to obtain numerical values as shown below:

Table 9

| | Skin Roughness (Dry Scaling Change on Skin Surface) | | | |
|---|---|---|---|---|
| | Compound | Score | Number of Subjects | Inflammatory Change |
| Composition of the invention | a | 0.10 | 10 | No particular change |
| | b | 0 | 10 | |
| | c | 0 | 10 | |
| | d | 0 | 10 | |
| | e | 0 | 10 | |
| | f | 0 | 10 | |
| Comparative Compound | Sodium lauryl sulfate | 3.06 | 36 | 4/36 subjects |
| | Sodium alkylbenzene sulfonate | 1.46 | 12 | None |
| | Sodium dodecylbenzene sulfonate | 1.83 | 6 | " |
| | Sodium α-olefin sulfonate | 0.75 | 12 | " |
| | Sodium α-dodecene sulfonate | 4.75 | 4 | " |
| | Sodium dodecylpolyoxyethylene sulfate | 0.46 | 12 | " |
| | Sodium dodecyl dioxyethylene sulfate | 2.00 | 6 | " |
| | Sodium laurate | 2.50 | 12 | 7/12 subjects |
| | Sodium myristate | 0.58 | 6 | None |
| | Water | 0 | 36 | " |

It is apparent from Table 9 that the compositions of the present invention exhibit remarkably reduced skin roughness or they scarcely exhibit the property of causing roughness, whereas the comparative surfactants heretofore employed exhibit the property of causing roughness.

EXAMPLE 4

The following mixtures (A)-(D) containing compounds of the present invention were prepared and the detergencies of them were determined according to a technique described below. For comparison, mixtures (E)-(J) containing conventional typical surfactants for detergents and sodium sesquialkyl phosphates were also tested. The numerals given below indicate wt.% of respective components of the mixtures.

Detergency power was determined as described below (Improved Rinelts method; J. Am. Chem. Soc., Vol. 33, P. 119).

As a specimen of oily matter, a mixture of 10 g of triolein, 5 g of cholesterol, 5 g of squalene and 5 g of palmitic acid was used. 25 grams of the mixture were dissolved in 25 ml of chloroform and the solution was attached uniformly to six glass slides for microscopic examination at 40° C., the quantity of the solution being controlled so that 0.4 ± 0.05 g was attached to the six glass slides. The washing device comprised a plastic holder containing the six glass slides fixed in a beaker (150 mm, diameter; 90 mm height) in which a propeller was set at the center. The propeller had stainless steel flat blades of a diameter of 35 mm.

Washing conditions:
Washing liquid: 900 ml (main active ingredient conc.: 0.2, 0.5, 1.0 and 3.0%)
Washing time: 10 or 30 minutes
Washing temperature: 40 ± 10° C.
Rotation of propeller: 13000 ± 100 rpm After completion of the washing, the glass plates were rinsed lightly by immersing them in deionized water five times and then dried under vacuum for 24 hours. The weights of the respective groups (each group comprised 6 glass plates) of the samples were determined before and after the deterging. Detergency was determined by the following equation:

$$R = (S_1 - S_w/S_1) \times 100$$

wherein R indicates deterging power (%), $S_1$ indicates amount (g) of oil attached to the plates before deterging and $S_w$ indicates amount (g) of oil attached to the plates after deterging. The results are shown in Table 10.

| Mixtures of the invention) | |
|---|---|
| Mixture A: | |
| Monosodium monolauryl phosphate | 25% |
| Water | Balance |
| Mixture B: | |
| Monosodium monodecyl phosphate | 25% |
| Water | Balance |
| Mixture C: | |
| Mono-triethanolamine salt of monolauryl phosphate | 25% |
| Water | Balance |
| Mixture D: | |
| Monosodium monolauryl phosphate | 25% |
| Lauryl sulfobetaine | 5% |
| Water | Balance |
| (Comparative mixtures) | |
| Mixture E: | |
| Sodium lauryl sulfate | 25% |
| Water | Balance |
| Mixture F: | |
| Sodium sesquilauryl phosphate* | 25% |
| Water | Balance |
| Mixture G: | |
| Triethanolamine salt of lauryl sulfate | 25% |
| Lauric acid diethanolamide | 2% |
| Laurylbetaine | 2% |
| Water | Balance |
| Mixture H: | |
| Sodium alkylbenzene sulfonate | 25% |
| Lauric acid diethanolamide | 2% |
| Water | Balance |
| Mixture I: | |
| Sodium α-olefin sulfonate | 25% |
| Water | Balance |
| Mixture J: | |
| Sodium dodecylpolyoxyethylene sulfate | 25% |
| Laurylbetaine | 5% |
| Water | Balance |

*General term for alkyl phosphate salts obtained from $P_2O_5$ and long chain aliphatic alcohols in a usual manner.

Table 10

| Deterging Rates of Various Mixtures | | | |
|---|---|---|---|
| Mixture | Conc. (wt. %) | Time (mins.) | Deterging Rate (%) |
| Mixture of the Invention A | 0.5 | 10 | 11.4 |
| | 1.0 | 10 | 15.3 |
| | 3.0 | 10 | 23.3 |
| | 0.2 | 30 | 40.1 |
| | 0.5 | 30 | 49.7 |
| | 1.0 | 30 | 58.6 |
| B | 0.5 | 10 | 11.8 |
| | 1.0 | 10 | 17.3 |
| | 3.0 | 10 | 22.6 |

Table 10-continued
Deterging Rates of Various Mixtures

| Mixture | | Conc. (wt. %) | Time (mins.) | Deterging Rate (%) |
|---|---|---|---|---|
| | | 0.2 | 30 | 25.4 |
| | | 0.5 | 30 | 39.8 |
| | | 1.0 | 30 | 48.2 |
| | | 0.5 | 10 | 17.8 |
| | | 1.0 | 10 | 19.9 |
| | C | 3.0 | 10 | 51.6 |
| | | 0.2 | 30 | 22.7 |
| | | 0.5 | 30 | 48.8 |
| | | 1.0 | 30 | 73.7 |
| | D | 0.5 | 30 | 29.1 |
| | | 1.0 | 30 | 47.1 |
| Comparative | | 0.5 | 10 | 18.5 |
| Mixture | | 1.0 | 10 | 26.5 |
| | E | 3.0 | 10 | 51.4 |
| | | 0.2 | 30 | 44.7 |
| | | 0.5 | 30 | 48.5 |
| | | 1.0 | 30 | 63.0 |
| | F | 1.0 | 30 | 32.0 |
| | G | 1.0 | 30 | 64.5 |
| | | 0.5 | 10 | 38.1 |
| | H | 1.0 | 10 | 43.8 |
| | | 3.0 | 10 | 47.7 |
| | I | 0.5 | 10 | 82.9 |
| | | 3.0 | 10 | 94.0 |
| | | 0.5 | 10 | 24.1 |
| | J | 1.0 | 10 | 23.9 |
| | | 3.0 | 10 | 28.7 |
| | Water | — | 10 | 0 |
| | | — | 30 | 0 |

It is apparent from Table 10 that the compositions of the present invention show substantially equivalent detergency to those of conventional detergent compositions, whereas sodium sesquialkyl phosphate showed little detergency.

For examining the property of compounds (A)–(J) to cause skin roughness, the circulation process was carried out in the same manner as described above except that the dilution was 1/25, whereby to determine indexes of skin roughness. The results are shown in Table 11.

Table 11
Skin Roughness Caused by Various Mixtures

| | Mixture | Score | Number of Subjects | Inflammatory Change |
|---|---|---|---|---|
| Mixture | A | 0.10 | 10 | |
| of the | B | 0 | 10 | No particular |
| Invention | C | 0 | 10 | change |
| | D | 0 | 10 | |
| Comparative | E | 3.06 | 36 | 4/36 |
| Mixture | F | 0 | 10 | None |
| | G | 2.43 | 10 | " |
| | H | 1.30 | 10 | " |
| | I | 0.75 | 12 | " |
| | J | 0.50 | 10 | " |

It is apparent from Table 11 that the mixtures containing the detergents of the present invention exhibit a very low property of causing skin roughness or exhibit said property only a little as compared with the conventional detergent mixtures.

It is also apparent from Examples 3 and 4 that the preparation of detergent compositions which possess an excellent detergency but do not cause skin roughness substantially is possible by employing the compounds of the invention, whereas it has been very difficult to obtain both excellent detergency and a very low degree of skin roughness by using known surfactants.

EXAMPLE 5

Shampoos comprising the following mixtures (M)–(S) containing compounds of the invention were prepared. Their foaming powers and foam stability were determined by Ross-Miles method at 40° C. and at a dilution of 1/40. For comparison, shampoos (T)–(Y) containing typical ordinary anionic surfactants or mixtures of monoalkyl phosphate salts and dialkyl phosphate salts not within the scope of the invention were tested in the same manner. The results are shown in Table 12.

(Shampoos of the invention)

Shampoo (M)
| | |
|---|---|
| Monosodium monomyristyl phosphate | 15% |
| Perfume | 0.3% |
| Water | Balance |

Shampoo (N)
| | |
|---|---|
| Monosodium monolauryl phosphate | 13% |
| Sodium dilauryl phosphate | 1% |
| Perfume | 0.3% |
| Water | Balance |

Shampoo (O)
| | |
|---|---|
| Mono-triethanolamine salt of monolauryl phosphate | 14% |
| Triethanolamine salt of dilauryl phosphate | 2% |
| Propylene glycol | 3% |
| Perfume | 0.3% |
| Water | Balance |

Shampoo (P)
| | |
|---|---|
| Monopotassium monomyristyl phosphate | 15% |
| Potassium dimyristyl phosphate | 2% |
| Glycerol | 2% |
| Perfume | 0.3% |
| Water | Balance |

Shampoo (Q)
| | |
|---|---|
| Di-triethanolamine salt of monomyristyl phosphate | 12% |
| Ethanol | 2% |
| Perfume | 0.3% |
| Water | Balance |

Shampoo (R)
| | |
|---|---|
| Monopotassium monomyristyl phsophate | 15% |
| Glycerol | 5% |
| Perfume | 0.3% |
| Water | Balance |

Shampoo (S)
| | |
|---|---|
| Monosodium monomyristyl phosphate | 12% |
| Sodium dimyristyl phosphate | 3% |
| Propylene glycol | 3% |
| Perfume | 0.3% |
| Water | Balance |

(Comparative Shampoos)

Shampoo (T)
| | |
|---|---|
| Sodium lauryl sulfate | 12% |
| Perfume | 0.3% |
| Water | Balance |

Shampoo (U)
| | |
|---|---|
| Triethanolamine salt of lauryl sulfate | 12% |
| Propylene glycol | 2% |
| Perfume | 0.3% |
| Water | Balance |

Shampoo (V)
| | |
|---|---|
| Sodium lauryl polyoxyethylene sulfate | 16% |
| Glycerol | 2% |
| Perfume | 0.3% |
| Water | Balance |

Shampoo (W)
| | |
|---|---|
| Sodium dodecylbenzene sulfonate | 15% |
| Glycerol | 5% |
| Perfume | 0.3% |
| Water | Balance |

Shampoo (X)
| | |
|---|---|
| Sodium α-myristyl sulfonate | 14% |
| Propylene glycol | 3% |

-continued

| | |
|---|---|
| Perfume | 0.3% |
| Water | Balance |
| Shampoo (Y) | |
| Disodium monolauryl phosphate | 16% |
| Sodium dilauryl phosphate | 8% |
| Glycerol | 3% |
| Perfume | 0.3% |
| Water | Balance |

Table 12

| | | Foaming Power (Ross-Miles test; 40° C, 1/20 dilution) | | | |
|---|---|---|---|---|---|
| | | Height of Foams | | | Foam Stability % |
| | | Immediately after treatment | After one min. | After five mins. | |
| Shampoos of the Invention | M | 241 | 220 | 213 | 88.4 |
| | N | 194 | 177 | 171 | 88.1 |
| | O | 212 | 193 | 187 | 88.3 |
| | P | 200 | 183 | 180 | 90.0 |
| | Q | 195 | 178 | 165 | 85.1 |
| | R | 215 | 196 | 190 | 88.4 |
| | S | 228 | 209 | 207 | 90.8 |
| Comparative Shampoo | T | 207 | 197 | 192 | 92.8 |
| | U | 205 | 187 | 180 | 87.8 |
| | V | 188 | 179 | 175 | 93.1 |
| | W | 200 | 185 | 183 | 91.5 |
| | X | 207 | 203 | 186 | 89.8 |
| | Y | 57 | 54 | 53 | 93 |

It is apparent from Table 12 that the shampoo compositions of the invention have foaming powers equivalent to or higher than those of ordinary shampoo compositions, while only a poor foaming power can be observed if the amount of dialkyl phosphate salt in the mixture thereof with monoalkyl phosphate salt is more than 20%.

In order to learn the feel of the compositions during the shampooing and the condition of the hair after shampooing, mixtures (M)-(S) and (T)-(Y) were subjected to shampoo tests.

As a result, it was found that, compared with conventional shampoos, the shampoos of the invention had a soft and wet foaming feeling and combing of hair after the shampoo was easy.

For examining the irritation of the skin caused by mixtures (M)-(Y), accomulative open patch tests on guinea pigs were effected in the same manner as described above; the dilution being 1/10. The results are shown in Table 13.

It is apparent from Table 13 that all mixtures containing active ingredients according to the invention exhibit only a very small skin irritative property or they cause much less skin irritation, as compared with ordinary shampoo mixtures.

Table 13

| | | Skin Irritation | |
|---|---|---|---|
| | | Accumulative open patch Skin irritation | 24 Hours closed patch Skin irritation |
| Shampoos of the Invention | M | 0.5 | 0 |
| | N | 0 | 0 |
| | O | 2.5 | 1.0 |
| | P | 2.0 | 0.5 |
| | Q | 1.0 | 0.5 |
| | R | 1.0 | 0.5 |
| | S | 2.0 | 1.0 |
| Comparative Shampoos | T | 21.0 | 28.0 |
| | U | 25.5 | 12.5 |
| | V | 10.0 | 8.0 |
| | W | 13.5 | 9.0 |
| | X | 11.5 | 8.5 |
| | Y | 2.5 | 2.0 |

EXAMPLE 6

Solid syndet bars (toilet soap bars) (a)-(c) containing compounds of the invention and (d)-(f) containing typical conventional surfactants were prepared. The foaming properties of the syndet bars were evaluated functionally.

| | |
|---|---|
| (Solid syndet bars of the invention) | |
| Syndet bar (a): | |
| Monosodium monolauryl phosphate | 90% |
| Perfume | 1% |
| Water | Balance |
| Syndet bar (b): | |
| Monosodium monodecyl phosphate | 85% |
| Sodium didecyl phosphate | 5% |
| Perfume | 1% |
| Water | Balance |
| Syndet bar (c): | |
| Monosodium monolauryl phosphate | 60% |
| Sodium dilauryl phosphate | 5% |
| Disodium monomyristyl phosphate | 20% |
| Perfume | 1% |
| Water | Balance |
| (Comparative syndet bar) | |
| Syndet bar (d): | |
| Sodium salts of coconut oil fatty acids | 40% |
| Sodium salts of beef tallow fatty acids | 45% |
| Perfume | 1% |
| Water | Balance |
| Syndet bar (e): | |
| Sodium lauryl sulfate | 90% |
| Perfume | 1% |
| Water | Balance |
| Syndet bar (f): | |
| Monosodium monolauryl phosphate | 55% |
| Sodium dilauryl phosphate | 35% |
| Perfume | 1% |

Syndet bars (a)-(e) exhibited excellent foaming properties and gave a nice feeling after the deterging. However, syndet bar (f) hardly produced foams and was poorly soluble in water.

For examining the skin irritation caused by mixtures (a)-(f), a 24 hour closed patch test on guinea pigs was effected in the same manner as above; the dilution being 1/100. The results are shown in Table 14.

Table 14

| | | Skin Irritation |
|---|---|---|
| | | Skin irritation |
| syndet bar of the invention | (a) | 0 |
| | (b) | 0.5 |
| | (c) | 0 |
| syndet bar of the invention | (d) | 12.5 |
| | (e) | 25.0 |
| | (f) | 1.5 |

It is apparent from Table 14 that the mixtures containing the active ingredients of the invention exhibited far less irritation as compared with ordinary syndet bar compositions or the former mixtures were substantially non-irritative.

It is apparent from Examples 5-6 that, although it is difficult to obtain both excellent foaming properties and non-irritation of the skin by using known surfactants, it is possible to obtain non-irritative detergent compositions without losing their detergencies by using the compounds of the present invention.

An amount of a phosphate to be contained in a detergent composition of this invention ranges from 0.2% by weight to 99.5% by weight.

Furthermore, this invention provides the following specific compositions. Percentages referred to are based on weight.

A shampoo composition consists essentially of 1.0 to 40.0%, preferably 10 to 23%, of the phosphate, 1 to 10% of a solubilizer selected from ethanol, urea, isopropanol, and polyols such as glycerine, ethylene glycol and propylene glycol, 0.1 to 40% of a foam stabilizer or booster selected from $C_{12}$-$C_{18}$ higher alcohols, ethoxylated products thereof, nonionic surfactants such as $C_{12}$-$C_{18}$ alkylolamides and $C_{12}$-$C_{18}$ higher alcohol ethoxylates, anionic surfactants such as $C_{12}$-$C_{18}$ alkyl sulfates, $C_{12}$-$C_{18}$ alkyl-monoglyceride sulfates, ethoxylated alkyl ($C_{12}$-$C_{18}$) sulfates, alkyl ($C_{12}$-$C_{18}$) benzene sulfonates and alpha-olefin ($C_{12}$-$C_{20}$) sulfonates and amphilic surfactants such as alkyl ($C_{12}$-$C_{18}$) betaine, alkyl ($C_{12}$-$C_{18}$) sulfobetain, alkyl ($C_{12}$-$C_{18}$) alanine and alkyl ($C_{12}$-$C_{18}$) imidazoline, 0.1 to 5% of a thickening agent selected from water-soluble polymers such as CMC, HEC, PVA (polyvinyl alcohol), PEG (polyethylene glycol) and polyacrylic acid and inorganic salts such as NaCl, NH$_4$Cl, and Na$_2$SO$_4$, 1 to 3% of a superfatting agent selected from higher alcohols ($C_{12}$-$C_{18}$), higher aliphatic acids ($C_{12}$-$C_{18}$), nonionic surfactants such as $C_{12}$-$C_{18}$ aliphatic monoglyceride, and $C_{12}$-$C_{18}$ ethoxylated higher alcohols, animal and vegetable oils, triglyceride, hydrocarbons such as liquid paraffin and squalane and higher esters such as ethylene glycol distearate (EGDS) and ethylene glycol monostearate (EGMS). The composition may contain 0.001 to 5% of a known sterilizing agent, antiseptics, ultraviolet-ray absorbant, chelating agent, anti-dandruff, antioxidant, dispersing agent, coloring matter, perfume or anti-flame agent. The composition may further contain 1-40% of an anionic or amphoteric surfactant as foaming agent, for example, $C_{12}$-$C_{18}$ alkyl sulfate (AS), ethoxylated product thereof, alkyl ($C_{12}$-$C_{18}$) monoglyceride sulfates (MS), α-olefin ($C_{12}$-$C_{20}$) sulfonates (AOS), alkyl ($C_{12}$-$C_{18}$) benzene sulfonates (ABS), alkyl ($C_{12}$-$C_{18}$) betain (AB), alkyl ($C_{12}$-$C_{18}$) sulfobetain (SB), alkyl ($C_{12}$-$C_{18}$) alanine (AA) and alkyl ($C_{12}$-$C_{18}$) imidazoline (AI).

A dentifrice composition consists essentially of 0.2 to 5.0%, preferably 0.8 to 4.0% of the phosphate, 5 to 70% of an abrasive selected from calcium hydrogen phosphate, calcium carbonate, alumina and calcium pyrophosphate, 0.3 to 5.0% of a binder selected from CMC (sodium carboxymethyl cellulose), HEC (hydroxyethyl cellulose), xanthan gum, hectorite, sodium alginate, locust bean gum, and montmorillonite, 5 to 40% of a humectant selected from propyleneglycol, glycerin and sorbitol, 0.1 to 0.3% of a sweetening material such as sodium saccharide, and optionally 0.001 to 1.0% of a known sterilizing agent, anti-flame agent, antiseptic, coloring matter or perfume, optionally containing 0.2 to 5.0% of anionic or amphoteric surfactants such as defined in the shampoo composition.

A syndet bar composition consists essentially of 0.5 to 99.5%, preferably 40 to 99.5%, of the phosphate, 1 to 20% of a binder selected from $C_{12}$-$C_{18}$ higher alcohols and ethoxylated product thereof, 0.5 to 50% of a foam stabilizer or booster (co-surfactant) selected from nonionic surfactancts such as polyoxyethylene-alkyl ($C_{12}$-$C_{18}$) ether, $C_{12}$-$C_{18}$ fatty acid ester of POE and $C_{12}$-$C_{18}$ alkylolamide (AM), anionic surfactants such as AS, MS, ABS, ethoxylated alcohol ($C_{12}$-$C_{18}$) sulfate (ES), and AOS, and amphilic surfactants such as AB, SB, AA and AI, 0.01 to 2% of a thickening agent selected from water-soluble polymers such as PEG, PVA, CMC, HEC and acrylic polymer optionally 0.001 to 2% of a known sterilizer, anti-flame agent, antiseptic, antioxidant, coloring matter of perfume and optionally 0.5 to 99.5% of anionic or amphoteric surfactants such as defined in the shampoo composition.

A detergent composition consists essentially of 5.0 to 95.0%, preferably 10 to 23%, of the phosphate, 5 to 50% of the first builder selected from sodium tripolyphosphate (STPP), sodium or potassium pyrophosphate, nitrilotriacetate (NTA), ethylenediamine tetraacetate (EDTA), alkanol ($C_{12}$-$C_{18}$) amines such as triethanolamine (TEA) and monoethanolamine (MEA), sodium silicate, sodium sulfate, sodium or potassium carbonate and sodium hydrogencarbonate, 1 to 5% of the second builder selected from water-soluble polymer such as PEG, PVA, CMC and polyacrylate, optionally 0.001 to 2% of an known antioxidant, coloring matter or perfume and optionally 0.5 to 99.5% of anionic or amphoteric surfactants such as defined in the shampoo composition.

A dish washing composition consists essentially of 1.0 to 40.0%, preferably 10 to 23% of the phosphate, 0.5 to 20% of a solubilizer selected from sodium para-toluene sulfonate (PTS), sodium metaxylene sulfonate (MXS), urea, ethanol, isopropylalcohol (IPA) and polyols such as propylene glycol (PG), ethylene glycol (EG), and glycerin (G), 1 to 20% of a booster selected from nonionic surfactants such as amide, amineoxide and emulgen, anionic surfactants such as AS, ES, AOS, ABS and MS and amphilic surfactants such as defined in the shampoo composition, 0.1 to 5% of a superfatting agent such as defined in the shampoo composition and optionally 0.5 to 99.5% of anionic or amphoteric surfactants such as defined in the shampoo composition.

The embodiments of the invention in which an exclusive property or privilege is claimed are defined as follows:

1. A detergent composition which has a low irritation effect on human skin, in which the organic surfactant component consists essentially of (A) from 100 to 80 weight percent of monoalkyl or monoalkenyl phosphate salt having the formula

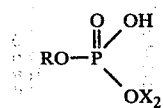

and (B) the balance of from zero to 20 weight percent is dialkyl or dialkenyl phosphate salt having the formula

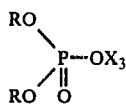

wherein R is alkyl or alkenyl having an average of from 10 to 16 carbon atoms, $X_3$ is hydrogen, alkali metal selected from the group consisting of sodium, potassium and lithium, ammonium, alkyl ($C_1$ to $C_3$) ammonium or hydroxyalkyl ($C_1$ to $C_3$) ammonium, and $X_2$ is said alkali metal, ammonium, alkyl ($C_1$ to $C_3$) ammonium or hydroxyalkyl ($C_1$ to $C_3$) ammonium, with the provisos: that said salts have a Krafft point of less than 55° C.; and that aqueous solutions of said salts have a pH of from 5 to 9.

2. A detergent composition as claimed in claim 1 in which the weight ratio of A:B is 100:0 to 90:10.

3. A detergent composition as claimed in claim 1 in which the weight ratio of A:B is substantially 100:0.

4. A detergent composition as claimed in claim 1 in which R is alkyl having an average of from 10 to 14 carbon atoms.

5. A detergent composition as claimed in claim 1 in which R is alkenyl having an average of 16 carbon atoms.

6. A detergent composition according to claim 1 in which said alkali metal is sodium or potassium.

7. A detergent composition according to claim 1 in which said alkyl ($C_1$ to $C_3$) ammonium is selected from the group consisting of trimethylammonium, triethylammonium, dibutylammonium, butyldimethylammonium and isopropyldimethylammonium and said hydroxyalkyl ($C_1$ to $C_3$) ammonium is selected from the dimethylmonoethanolammonium, methyldiethanolammonium, monoethanolammonium, diethanolammonium, triethanolammonium and isopropylethanolammonium.

8. A detergent composition according to claim 1 in which said hydroxyalkyl ($C_1$ to $C_3$) ammonium is monoethanolammonium, diethanolammonium or triethanolammonium.

9. A detergent composition consisting essentially of 5.0 to 95.0% of said phosphate salt organic surfactant component as claimed in claim 1, 5 to 50% of water-soluble detergent builder salt, and from 1 to 5% of a water-soluble polymer selected from the group consisting of polyethylene glycol, polyvinyl alcohol, carboxymethyl cellulose and polyacrylate.

10. A dish washing composition consisting essentially of 1.0 to 40.0% of said phosphate salt organic surfactant component as claimed in claim 1, 0.5 to 20% of a solubilizer selected from the group consisting of sodium paratoluene sulfonate, sodium metaxylene sulfonate, urea, ethanol, isopropyl alcohol, propylene glycol, ethylene glycol, and glycerin, 1 to 20% of a booster selected from the group consisting of water-soluble, synthetic, organic nonionic surfactants, water-soluble, synthetic, organic anionic surfactants and water-soluble, synthetic, organic amphilic surfactants, and 0.1 to 5% of a superfatting agent.

11. A detergent composition as claimed in claim 1 in which R has an average of 12 carbon atoms derived from coconut oil.

12. A detergent composition as claimed in claim 11 in which $X_2$ is triethanolammonium, sodium or potassium.

13. A method of cleaning which comprises applying to a substrate to be cleaned, water and a material consisting essentially of (A) from 100 to 80 weight percent of monoalkyl or monoalkenyl phosphate salt having the formula

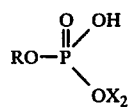

and (B) the balance of from zero to 20 weight percent is dialkyl or dialkenyl phosphate salt having the formula

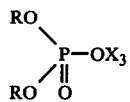

wherein R is alkyl or alkenyl having an average of from 10 to 16 carbon atoms, $X_3$ is hydrogen, alkali metal selected from the group consisting of sodium, potassium and lithium, ammonium, alkyl ($C_1$ to $C_3$) ammonium or hydroxyalkyl ($C_1$ to $C_3$) ammonium, and $X_2$ is said alkali metal, ammonium, alkyl ($C_1$ to $C_3$) ammonium or hydroxyalkyl ($C_1$ to $C_3$) ammonium, with the provisos: that said salts have a Krafft point of less than 55° C.; and that aqueous solutions of said salts have a pH of from 5 to 9, said material being effective as a water-soluble organic surfactant for cleaning said substrate.

* * * * *